(12) United States Patent
Shackelford et al.

(10) Patent No.: US 6,254,621 B1
(45) Date of Patent: Jul. 3, 2001

(54) CLOSED CHANNEL RETRACTABLE SURGICAL BLADE DEVICE AND ASSOCIATED METHOD

(75) Inventors: Howard L. Shackelford, Triadelphia, WV (US); Thomas D. Nickerson, Meadville; John P. Gratton, Erie, both of PA (US)

(73) Assignee: S & S Surgical Products, Inc., Meadville, PA (US)

( * ) Notice: Subject to any disclaimer, the term of this patent is extended or adjusted under 35 U.S.C. 154(b) by 0 days.

(21) Appl. No.: 09/585,304

(22) Filed: Jun. 1, 2000

(51) Int. Cl.[7] .................................................. A61B 17/32
(52) U.S. Cl. ............................................. 606/167; 30/162
(58) Field of Search .................................. 606/167, 185; 30/162, 335, 337, 339

(56) References Cited

U.S. PATENT DOCUMENTS

| | | |
|---|---|---|
| D. 264,799 | 6/1982 | Osada . |
| D. 264,800 | 6/1982 | Osada . |
| D. 264,801 | 6/1982 | Osada . |
| D. 264,803 | 6/1982 | Machida . |
| 2,285,155 | 6/1942 | Frost . |
| 2,413,082 | 12/1946 | Skaer . |
| 4,089,112 | 5/1978 | Richards . |
| 4,103,421 | 8/1978 | Quenot . |
| 4,499,898 | 2/1985 | Knepshield et al. . |
| 4,615,118 | 10/1986 | Ihata . |
| 4,729,168 | 3/1988 | Yeh . |
| 4,735,202 | 4/1988 | Williams . |
| 5,071,426 | 12/1991 | Dolgin et al. . |
| 5,099,578 | 3/1992 | Jan . |
| 5,201,748 | 4/1993 | Newman et al. . |
| 5,207,696 | 5/1993 | Matwijcow . |
| 5,250,063 | 10/1993 | Abidin et al. . |
| 5,258,001 | 11/1993 | Corman . |
| 5,330,493 | * 7/1994 | Haining ................................ 606/167 |
| 5,403,337 | 4/1995 | Platts . |
| 5,475,925 | * 12/1995 | Newman et al. ...................... 30/162 |
| 5,497,553 | * 3/1996 | Chong ................................... 30/162 |
| 5,531,754 | 7/1996 | Shackelford, Sr. et al. . |
| 5,599,351 | * 2/1997 | Haber et al. ......................... 606/167 |
| 5,626,596 | * 5/1997 | DeSatnick ............................ 606/170 |

FOREIGN PATENT DOCUMENTS

| | | |
|---|---|---|
| 2617148 | 10/1977 | (DE) . |
| 2648423 | 4/1978 | (DE) . |
| 3722899 | 1/1989 | (DE) . |
| 2113550 | 8/1983 | (GB) . |

* cited by examiner

Primary Examiner—Kennedy Schaetzle
Assistant Examiner—Kristen Droesch
(74) Attorney, Agent, or Firm—David C. Jenkins; Eckert Seamans Cherin & Mellott, LLC

(57) ABSTRACT

A retractable surgical blade includes a handle defining a channel and a surgical blade member. The handle has a front portion and a back portion. The front portion defines a channel which confines the surgical blade member. The back portion includes a front wall and may be solid. The surgical blade member includes a slider to which is secured a surgical blade. The slider has a portion which engages the channel so that the surgical blade member can move from a cutting position in which the surgical blade projects from the handle and can be employed in a surgical procedure to a parked position in which the surgical blade is disposed in the channel. When in the parked position, the surgical blade is unable to cut or stab persons associated with the surgical procedure. The device may include a locking device to lock the surgical blade member in the parked position. An associated method of performing a surgical procedure is also disclosed.

25 Claims, 3 Drawing Sheets

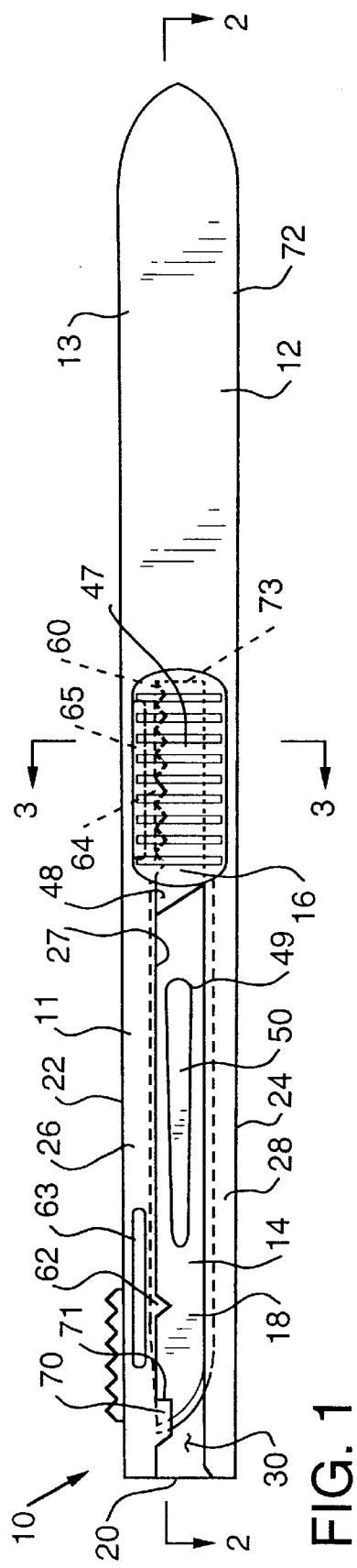
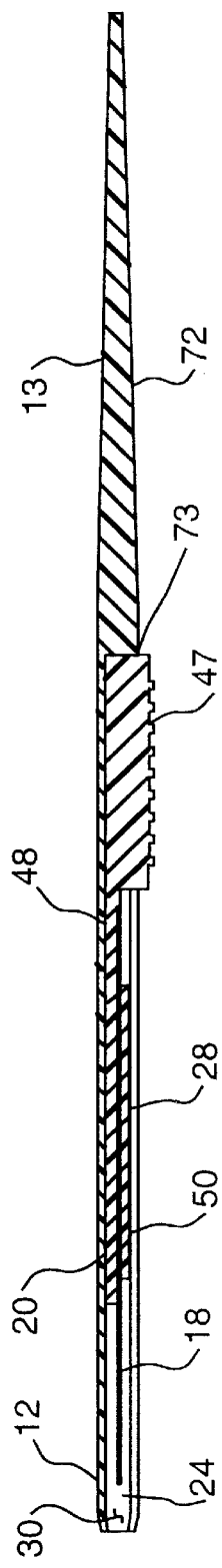
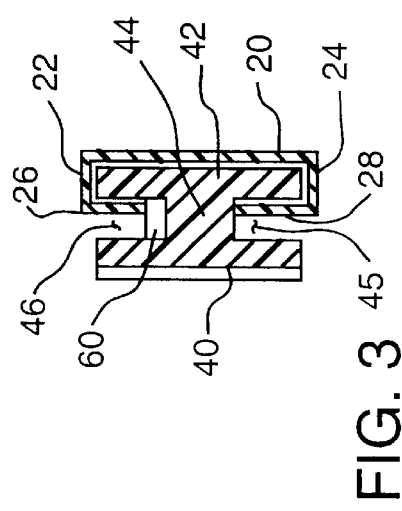

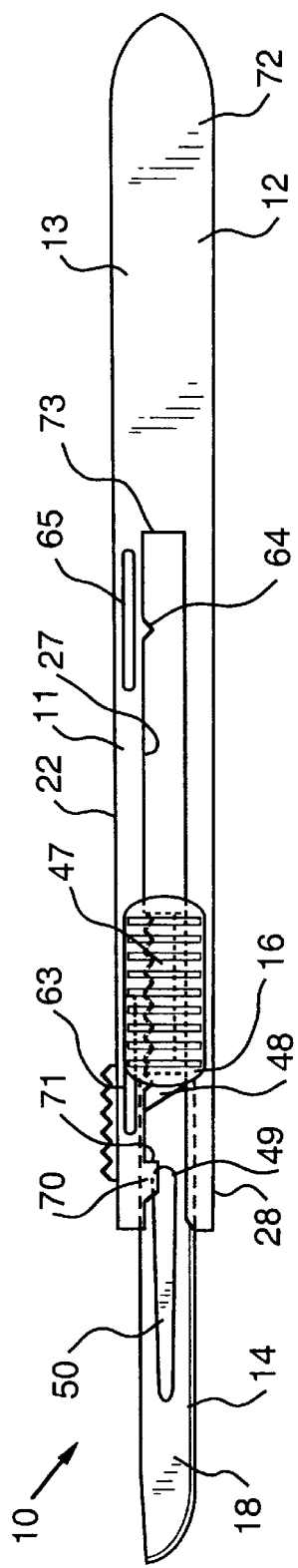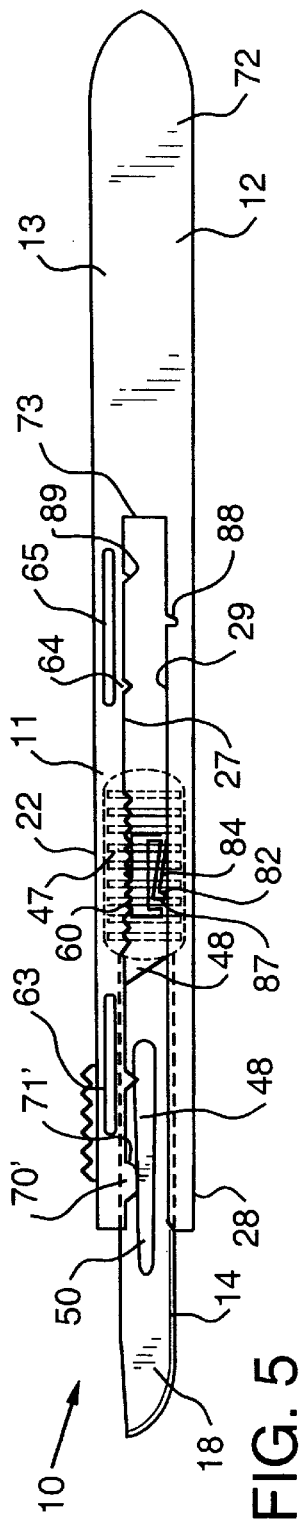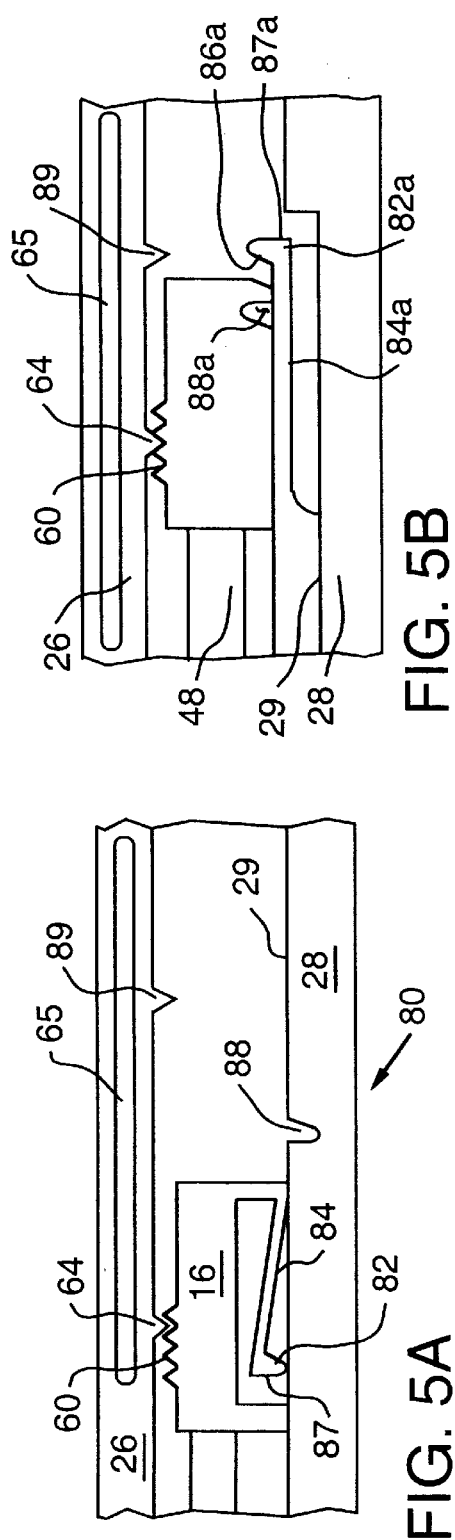

CLOSED CHANNEL RETRACTABLE SURGICAL BLADE DEVICE AND ASSOCIATED METHOD

BACKGROUND OF THE INVENTION

1. Field of the Invention

This invention relates to a retractable surgical blade device and an associated method and, more specifically, to a retractable surgical blade device having a channel which is closed at one end.

2. Background Information

Surgical scalpels are well known devices used by surgeons and other medical personnel to make incisions into patients. These scalpels consist of a handle member, typically made of steel, and a removable surgical blade disposed on one end of the handle. The surgical blades, in order to be effective, are extremely sharp and must be handled carefully by all personnel involved in the surgical procedure in which the scalpel is used.

Because the scalpels have exposed blades, the chance of accidental stabbing or cutting of medical personnel is great. In addition to the injury caused by the cut or stab itself, infectious viruses and/or bacteria can enter into the cut or wound during the surgical procedure. Many infectious diseases can be transmitted from the blood of a surgical patient to an open wound of medical personnel inadvertently cut by the surgical blade of a scalpel.

Medical personnel may be protected from accidental scalpel wounds by a retractable surgical blade device such as the one disclosed in U.S. Pat. No. 5,531,754 which is incorporated by reference. The retractable surgical blade device includes a handle defining a channel, a blade member which is joined by a blade and a body member, or slider, and a stop means such as a plug or cantilevered end portion. The handle channel extends the entire length of the channel having open ends. The front end includes a stop which allows the blade to be extended therefrom while preventing the slider from passing therethrough. The back end is closed by the plug or cantilevered end portion which prevents the slider from passing therethrough.

While this design presents an elegant solution to the problem of exposed blades in during surgery, a disposable plastic retractable surgical blade, like any plastic device, can be improved and the manufacturing cost could be reduced by the elimination of any unnecessary parts, the elimination of any unnecessary molding or, the reduction of the number of manufacturing steps. Additionally, the retractable surgical blade device disclosed in U.S. Pat. No. 5,531,754 cannot be locked into a closed position following its final use. Such a locking device would ensure that the contaminated blade could not be easily re-extended and possibly cut someone.

There is, therefore, a need for a retractable surgical blade device having a reduced number of parts.

There is a further need for a retractable surgical blade device which can be assembled with fewer manufacturing steps.

There is a further need for a retractable surgical blade device which incorporates a locking device to lock the blade in a closed position following its final use.

SUMMARY OF THE INVENTION

These needs, and others, are met by the closed channel retractable surgical blade device. The device comprises a handle and a surgical blade member having a slider to which a surgical blade is secured. The handle has two portions: a front portion defining a channel and a back portion which may be solid. The slider has a portion which engages the channel so that the surgical blade member can move between (a) a cutting position in which the surgical blade projects from the handle to permit the device to be employed in a surgical procedure and (b) a parked position in which the surgical blade is disposed in the channel. When in the parked position, the surgical blade is unable to cut or stab persons associated with the surgical procedure. The retractable surgical blade device also includes a locking device to lock the blade in the parked position prior to disposal. The device further includes an improved structure of cooperating positioning members on the handle and the slider to position and secure the device in the desired position.

The method of the invention involves providing a retractable surgical blade device as described above in the parked position and moving the surgical blade member into the cutting position. A surgical procedure is then performed. The surgical blade member is then moved from the cutting position back into the parked position.

It is an object of the invention to provide a closed channel surgical blade device which reduces the cost of manufacture of such a retractable surgical blade device.

It is still a further object of the invention to provide a surgical blade device that can be safely locked in a parked position prior to disposal.

It is a further object of the invention to provide a surgical blade device that is easy to use.

It is still another object of the invention to provide a surgical blade device that is adapted to be used with different sizes and types of surgical blades.

It is still yet another object of the invention to provide a method of performing a surgical procedure using a retractable surgical blade device which can be locked in the parked position prior to disposal.

These and other objects of the invention will be more fully understood from the following description of the invention with reference to the drawings appended hereto.

BRIEF DESCRIPTION OF THE DRAWINGS

FIG. 1 is a top plan view of an embodiment of a closed channel retractable surgical blade device made in accordance with the invention.

FIG. 2 is a cross-sectional view taken along line 2—2 of FIG. 1.

FIG. 3 is a cross-sectional view taken along line 3—3 of FIG. 1.

FIG. 4 is a top plan view showing the device in the cutting position.

FIG. 5 is a top plan view of an alternate embodiment of a closed channel retractable surgical blade device made in accordance with the invention.

FIG. 5A is a detail view of the locking device.

FIG. 5B is a detail view of an alternate locking device.

DETAILED DESCRIPTION

Figure 6:
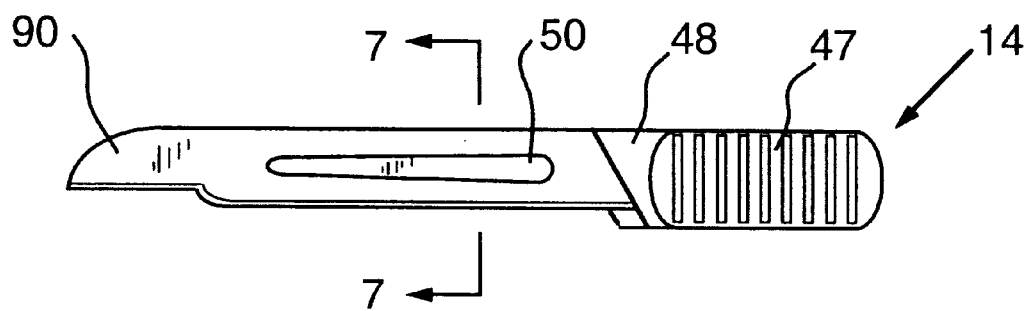
FIG. 6 is a top plan view of the surgical blade member showing a different surgical blade.

Referring now to FIGS. 1–3, a closed channel retractable surgical blade device 10 made in accordance with the invention is shown. The device 10 consists of a handle member 12 having two portions; a front portion 11 and a back portion 13. A surgical blade member 14 is adapted for slidable movement in the handle member 12. The surgical blade member 14 further consists of a slider 16 to which is secured a unitary surgical blade 18.

The handle member front portion 11 consists of a base wall 20, two elongated generally parallel longitudinal sidewalls 22 and 24 which extend generally perpendicularly from the longitudinal edges of the base wall 20 and two elongated longitudinal flanges 26 and 28 which extend generally perpendicularly from the longitudinal edges of the respective sidewalls 22 and 24. Each flange 26, 28 has a distal interior edge 27, 29 opposite sidewalls 22 and 24 respectively. The handle member front portion 11, therefore, defines a channel 30 in which the surgical blade member 14 is slidably movable. It will be appreciated that the handle member 12 can be made of any suitable material, such as steel or plastic, and can be either for a one-time use (disposable) or for multiple uses.

The handle member back portion 13 also includes the base wall 20 and the two elongated generally parallel longitudinal sidewalls 22 and 24 which extend generally perpendicularly from the longitudinal edges of the base wall 20, as well as a front wall 72. Front wall 72 extends between sidewalls 22 and 24 in a plane generally parallel to base wall 20. The front wall 72 may be joined with or integral to base wall 20. As shown in FIG. 2, the back portion 13 may be narrower than front portion 11.

As can best be seen in FIG. 3, the slider 16 has a cross-sectional shape of an "I-beam"0 consisting of a top portion 40, a bottom portion 42 and an interconnecting intermediate portion 44. The slider 16 shape defines a pair of opposed longitudinal slots 45, 46. Flanges 26 and 28 engage into slots 45, 46 respectively and cooperate to guide and maintain the surgical blade member 14 in the channel 30. The bottom portion 42 is disposed in the channel 30, while top portion 40 includes an engaging section which extends above the handle member 12 to facilitate grasping and moving the surgical blade member 14 in the channel 30. The engaging section has an engaging surface 47 which is preferably serrated in order to further enhance the users grip on the slider 16 of the surgical blade member 14. It will be appreciated that the slider 16 can be made of any suitable material such as steel or plastic and can also be designed for one-time (disposable) use or multiple uses.

The surgical blade 18 is secured to a flange portion 48 of the slider 16 as can best be seen in FIGS. 1 and 2. The surgical blade 18 defines an aperture 49 which is snap-fit onto a projection 50 disposed on flange portion 48. The surgical blade 18, therefore, can be easily removed and replaced by another surgical blade.

The surgical blade member 14 is shown in FIG. 1 in its "parked position." In this position, the surgical blade member 14 is retracted entirely into channel 30 thus the surgical blade 18 is not exposed. The surgical blade member 14 is held in the parked position by cooperating positioning members on the handle member 12 and the slider 16 of surgical blade member 14. The positioning members consist of a serrated edge 60 formed along one edge of intermediate portion 44. The serrated edge 60 cooperates with pawls 62, 64 which are formed in flange 26. The pawls 62, 64 are located between openings 63, 65 and the flange interior edge 27. The openings 63, 65 are sufficiently close to interior edge 27 and have a sufficient width so that the pawls 62, 64 may flex as the pawl 62, 64 engages serrated edge 60. The pawls 62, 64 are preferably located so as to be in the medial portion of the serrated edge 60 when the surgical blade member 14 is in either its parked position or cutting position (described below). While in the parked position, the device 10 can be handled by medical personnel and others and can be stored without the danger of the surgical blade 18 causing a stab or other type of wound.

The device 10 also has stop means located at both ends thereof The stop means on the front portion 11 consists of an extension section 70 of flange 26. As can be seen in FIG. 4, when the surgical blade member 14 is in the cutting position, the slider 16 abuts flat inner edge 71 of extension section 70 to prevent further outward movement of the surgical blade member 14. The flat inner edge 71 prevents the surgical blade member 14 from disengaging from the handle member 12 at the open end of the handle member 12. The back portion 13 stop means is consists of a blocking edge 73 on front wall 72 extending from sidewall 22 to sidewall 24. The blocking edge 73 prevents the surgical blade member 14 from disengaging from the handle member 12 at the right end of the handle member 12.

As shown in FIGS. 5 and 5A the device 10 may also include a locking device 80. While any type of locking device 80 may be used, in the preferred embodiment, the locking device 80 includes a pawl 82 mounted on an leaf spring 84 which is attached to the edge of intermediate portion 44 opposite serrated edge 60. The leaf spring 84 is attached to the intermediate portion 44 on the portion of the slider 16 proximal to blocking edge 73 and extends, preferably at an angle, towards flange portion 48. The leaf spring 84 terminates in a locking pawl 82. The locking pawl 82 has a locking surface 87 that is flat and substantially normal to interior edge 29. The interior edge 29 includes a notch 88 which has a shape that corresponds to locking pawl 82. The notch 88 is positioned to engage locking pawl 82 when slider 16 is placed in the locked position (described below). If the device 10 uses the locking device 80, the blocking edge 73 is not used as a stop means. Instead, an additional parking pawl 89 is located on flange interior edge 27 opposite notch 88. The resistance created by slider 16 contacting the parking pawl 89 prevents the user from accidentally locking the device 10 and stops the slider 16 in the parked position.

Alternatively, as shown in FIG. 5B, the leaf spring 84a may be located on sidewall 24. The leaf spring 84a extends from interior edge 29 and includes a locking pawl 82a. The locking pawl 82a has a sloped edge 86a proximal to front portion 11 and a flat edge 87a located proximal to back portion 13. The locking pawl 82a cooperates with a locking notch 88a located on one edge of the slider intermediate portion 44, preferably opposite serrated edge 60. The slider notch 88a is shaped to engage locking pawl 82a. The locking pawl is positioned to engage locking pawl 82 when slider 16 is placed in the locked position (described below).

In operation, when it is desired to use the device 10 in a surgical procedure, the engaging surface 47 is grasped preferably by a user's thumb and the surgical blade member 14 is extended to a "cutting position" shown in FIG. 4. In the cutting position, the surgical blade 18 is exposed and ready for use in a surgical procedure. It will be appreciated that the surgical blade member 14 slidably moves from the parked position shown in FIG. 1 to the cutting position shown in FIG. 4 by the user applying a force on the surgical blade member 14 to translate the surgical blade member 14 in the channel 30. The pawls 62, 64, because of the flexibility provided by openings 63, 65, slide over the serrated edge 60. During the surgical procedure the surgical blade member 14 may be moved between the cutting and parked positions as required to perform the procedure and to safely pass the device 10 from one person to another. When the surgical procedure is completed, the user merely slides the surgical blade member 14 back into the parked position. At this point, if desired, slightly more pressure can be applied to move slider 16 towards back portion 13. When the locking pawl 82 enters notch 88, flat edge 87 engages notch 88 and prevents the slider 16 from moving towards front portion 11. At this point, the entire device 10 can be disposed. When the device 10 is disposed of with the blade member 14 in the locked position, waste processing personnel are protected against inadvertent stab or cut wounds.

Additionally, as shown in FIG. 5, the front stop means, extension section 70, may be altered to allow the surgical blade member 14 to be removed through handle member front portion 11. The extension section may be molded with a sloped inner edge 71'. The extension 70 and flange 28 create resistance to blade member 14 passing beyond the cutting position. Thus, under normal pressure the blade member 14 will stop in the cutting position. Sloped inner edge 70', however, makes it possible to slide blade member 14 past extension section 70 and out of the handle 12. Once blade member 14 is disengaged from the handle 12, a different blade member 14, such as one with a different shaped blade (see below) may be inserted into the handle 12. Alternatively, the surgical blade 18 may be removed from the snap-fit projection 50 and a different blade may be installed.

Figure 7:
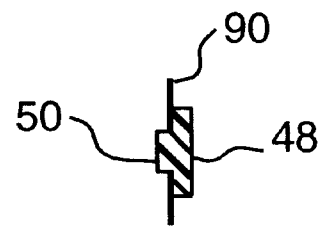
FIG. 7 is a cross-sectional view taken along line 7—7 of FIG. 5.

FIGS. 6 and 7 shows another embodiment of a surgical blade member in which like parts of surgical blade member 14 are labeled with like reference characters. The surgical blade member 14 of FIG. 6 has a different type of surgical blade 90 than was shown in FIGS. 1–4. As can be seen in FIG. 7, the blade 90 is snap fit onto the projection 50 in the flange portion 48 of slider 16 of the surgical blade member 14. It will be appreciated that the invention contemplates utilizing any type of surgical blade. Surgical blades are conventionally labeled with a number such as "10", "11", "15" etc. and have a standard sized aperture 49 which engages projection 50. The invention contemplates use with these standard sized blades but can also be modified to accommodate other sizes and types of surgical blades.

The method of the invention involves providing the retractable surgical blade device 10 as described above in the parked position and then moving the surgical blade member 14 into a cutting position in which the surgical blade 18 projects from the handle 12. Once in the cutting position, an incision is made into the patient and a surgical procedure is performed. After performing the surgical procedure, thy surgical blade member 14 is moved into the locked position so that the surgical blade is unable to cut or stab persons.

The device 10 shown in FIGS. 1–7 is preferably grasped by a user's right hand so that the users thumb can engage the engaging surface 47 to move the surgical blade member 14 in the channel 30. The invention contemplates also a left handed version of the device, which is essentially a mirror image of device 10, such that the device can be grasped and used efficiently with a user's left hand.

It will be appreciated that the closed channel retractable surgical blade device disclosed herein consists of fewer parts than the retractable surgical blade device disclosed in U.S. Pat. No. 5,531,754. As such, this device may be manufactured in a more cost efficient manner due to reduced material costs and assembly costs. Additionally, the device disclosed includes an added safety lock to lock the blade in a parked position.

Whereas particular embodiments of the invention have been described above for purposes of illustration, it will be evident to those skilled in the art that numerous variations of the details may be made without departing from the invention as defined in the appended claims.

What is claimed is:

1. A closed channel retractable surgical blade device comprising:

a handle having a front portion and a back portion;

said front portion including a base wall and a pair of opposed sidewalls extending generally perpendicularly from said base wall, said sidewalls each including a flange extending generally perpendicularly therefrom;

said base wall, said sidewalls and said flanges defining a channel;

a surgical blade member having a slider which defines a pair of opposed longitudinal slots and a surgical blade secured to said slider;

said flanges engaging into said slots to guide and maintain said surgical blade member in said channel;

said surgical blade member being movable between a cutting position wherein said surgical blade projects from said front end of said handle and said device can be employed in a surgical procedure and a parked position wherein said surgical blade is disposed in said channel so that said surgical blade is unable to cut or stab persons associated with a surgical procedure;

said handle includes a front end stop means comprising a section extending from said flange to resist said surgical blade member from disengaging from said front end of said handle;

said back portion including a base wall, a pair of opposed sidewalls extending generally perpendicularly from said base wall, and a front wall extending between the sidewalls in a plane generally parallel to the base wall;

a back portion stop means comprising a blocking edge on said front wall to prevent said surgical blade member from disengaging from said back end of said handle;

wherein said handle and said slider include positioning members, said positioning members positioning and securing said surgical blade in a desired position;

said positioning members include at least two pawls on one of said flanges and a serrated edge on said slider adapted to engage said pawls;

said flange including an opening adjacent to each said pawl; and wherein one said pawl engages the medial portion of said serrated edge when said surgical blade member is in said cutting position and another pawl engages the medial portion of said serrated edge when said surgical blade member is in said parked position.

2. The device of claim 1, wherein said surgical blade member is slidably movable in said channel between said parked position and said cutting position.

3. The device of claim 1, wherein said slider includes an engaging section, said engaging section being employed to move said surgical blade member in said channel.

4. The device of claim 3, wherein said engaging section includes an engaging surface having serrations in order to facilitate gripping thereof.

5. The device of claim 1, wherein said handle is made of materials selected from the group consisting of metal and plastic.

6. The device of claim 1, wherein said slider is made of materials selected from the group consisting of metal and plastic.

7. The device of claim 1, wherein said surgical blade member includes blade securing means for securing said surgical blade to said slider.

8. The device of claim 7, wherein said means for securing said surgical blade is a raised section on said slider and an aperture defined by said surgical blade, said raised section engaging into said aperture to snap-fit said surgical blade onto said slider.

9. The device of claim 1, wherein said front stop means is an extension with a sloped inner edge.

10. A closed channel retractable surgical blade device comprising:

a handle having a front portion and a back portion;
   said front portion including a base wall and a pair of opposed sidewalls extending generally perpendicularly from said base wall, said sidewalls each including a flange extending generally perpendicularly therefrom;
   said base wall, said sidewalls and said flanges defining a channel;
   a surgical blade member having a slider which defines a pair of opposed longitudinal slots and a surgical blade secured to said slider;
   said flanges engaging into said slots to guide and maintain said surgical blade member in said channel;
   said surgical blade member being movable between a cutting position wherein said surgical blade projects from said front end of said handle and said device can be employed in a surgical procedure and a parked position wherein said surgical blade is disposed in said channel so that said surgical blade is unable to cut or stab persons associated with a surgical procedure and a locked position wherein said surgical blade can no longer be extended into said cutting position;
   said handle includes a front end stop means comprising a section extending from said flange to resist said surgical blade member from disengaging from said front end of said handle;
   said back portion including a base wall, a pair of opposed sidewalls extending generally perpendicularly from said base wall, and a front wall extending between the sidewalls in a plane generally parallel to the base wall;
   a locking device;
   a back portion stop means comprising a parking pawl on one said flange to resist surgical blade member from engaging said locking device;
   said positioning members include at least two pawls on one of said flanges and a serrated edge on said slider adapted to engage said pawls; and
   said flange including an opening adjacent to each said pawls;
   wherein one said pawl engages the medial portion of said serrated edge when said surgical blade member is in said cutting position and another pawl engages the medial portion of said serrated edge when said surgical blade member is in said parked position.

11. The device of claim 10, wherein said locking device includes a leaf spring terminating in a locking pawl and a corresponding locking notch.

12. The device of claim 11, wherein said leaf spring is attached to said slider and said notch is located in one said flange.

13. The device of claim 11, wherein said leaf spring is attached to one said flange; and
   said notch is disposed on said slider.

14. The device of claim 11, wherein said surgical blade member is slidably movable in said channel between said parked position and said cutting position and may be moved into said locked position.

15. The device of claim 10, wherein said slider includes an engaging section, said engaging section being employed to move said surgical blade member in said channel.

16. The device of claim 15, wherein said engaging section includes an engaging surface having serrations in order to facilitate gripping thereof.

17. The device of claim 10, wherein said handle is made of materials selected from the group consisting of metal and plastic.

18. The device of claim 10, wherein said slider is made of materials selected from the group consisting of metal and plastic.

19. The device of claim 10, wherein said surgical blade member includes blade securing means for securing said surgical blade to said slider.

20. The device of claim 19, wherein said means for securing said surgical blade is a raised section on said slider and an aperture defined by said surgical blade, said raised section engaging into said aperture to snap-fit said surgical blade onto said slider.

21. The device of claim 10, wherein said front stop means is an extension with a sloped inner edge.

22. A method of performing a surgical procedure comprising the steps of:

providing a closed channel retractable surgical blade device comprising (i) a handle having a front portion and a back portion, said handle front portion including a base wall and a pair of opposed sidewalls extending generally perpendicularly from said base wall, said sidewalls each including a flange extending generally perpendicularly therefrom wherein said base wall, said sidewalls and said flanges define a channel and said back portion including a base wall, a pair of opposed sidewalls extending generally perpendicularly from said base wall, and a front wall extending between the sidewalls in a plane generally parallel to the base wall; (ii) a surgical blade member having a slider which defines a pair of opposed longitudinal slots and a surgical blade secured to said slider, said flanges engaging into said slots to guide and maintain said surgical blade member in said channel; (iii) said front portion includes a front end stop means comprising a section extending from said flange to resist said surgical blade member from disengaging from said front end of said handle and a back end stop means comprising blocking edge on said front wall to prevent said surgical blade member from disengaging from said back end of said handle; (iv) said handle and said slider include positioning members, said positioning members positioning and securing said surgical blade in a desired position; and (v) said positioning members include at least two pawls on one of said flanges and a serrated edge on said slider adapted to engage said pawls, said flange includes an opening adjacent to each said pawls, and wherein one said pawl engages the media portion of said serrated edge when said surgical blade member is in said cutting position and another pawl engages the medial portion of said serrated edge when said surgical blade member is in said parked position;

providing said device being in a parked position wherein said surgical blade is disposed in said channel;

moving said surgical blade member into a cutting position wherein said surgical blade projects from said front end of said handle;

performing a surgical procedure using said device while said surgical blade member is in said cutting position; and moving said surgical blade member back into said parked position wherein said surgical blade is retracted into said channel such that said surgical blade is unable to cut or stab persons associated with a surgical procedure.

23. The method of claim 22, including the step of:

after retracting said surgical blade member into said parked position, disposing of said device.

24. A method of performing a surgical procedure comprising the steps of:

providing a closed channel retractable surgical blade device comprising (i) a handle having a front portion and a back portion, said handle front portion including a base wall and a pair of opposed sidewalls extending generally perpendicularly from said base wall, said sidewalls each including a flange extending generally perpendicularly therefrom wherein said base wall, said sidewalls and said flanges define a channel and said back portion including a base wall, a pair of opposed sidewalls extending generally perpendicularly from said base wall, and a front wall extending between the sidewalls in a plane generally parallel to the base wall; (ii) a surgical blade member having a slider which defines a pair of opposed longitudinal slots and a surgical blade secured to said slider, said flanges engaging into said slots to guide and maintain said surgical blade member in said channel; (iii) said front portion includes a front end stop means comprising a section extending from said flange to resist said surgical blade member from disengaging from said front end of said handle and a back end stop means comprising blocking edge on said front wall to prevent said surgical blade member from disengaging from said back end of said handle; (iv) a locking device having a locking pawl and a locking notch; (v) said handle and said slider include positioning members, said positioning members positioning and securing said surgical blade in a desired position; and (vi) said positioning members include at least two pawls on one of said flanges and a serrated edge on said slider adapted to engage said pawls, said flange includes an opening adjacent to each said pawls, and wherein one said pawl engages the medial portion of said serrated edge when said surgical blade member is in said cutting position and another pawl engages the medial portion of said serrated edge when said surgical blade member is in said parked position;

providing said device being in a parked position wherein said surgical blade is disposed in said channel;

moving said surgical blade member into a cutting position wherein said surgical blade projects from said front end of said handle;

performing a surgical procedure using said device while said surgical blade member is in said cutting position; and moving said surgical blade member back into said parked position wherein said surgical blade is retracted into said channel such that said surgical blade is unable to cut or stab persons associated with a surgical procedure.

25. The method of claim 24, including the step of:

after retracting said surgical blade member into said parked position, engaging said locking device and disposing of said device.

* * * * *

UNITED STATES PATENT AND TRADEMARK OFFICE
CERTIFICATE OF CORRECTION

PATENT NO. : 6,254,621 B1
DATED : July 3, 2001
INVENTOR(S) : Howard L. Shackelford It is certified that error appears in the above-identified patent and that said Letters Patent is hereby corrected as shown below:

Column 3,
Line 30, ""I-beam"0" should be -- "I-beam" --.

Column 4,
Line 8, "thereof" should be -- thereof. --.

Column 5,
Line 54, "users" should be -- user's --.

Signed and Sealed this

Thirteenth Day of August, 2002

Attest:

Attesting Officer

JAMES E. ROGAN
Director of the United States Patent and Trademark Office